United States Patent
Toida et al.

[11] Patent Number: 5,496,949
[45] Date of Patent: Mar. 5, 1996

[54] PYRAZINE DERIVATIVES

[75] Inventors: Ichiro Toida, Sayama; Setsuko Yamamoto, Tokyo; Nanao Watanabe, Nara; Toshikazu Ura, Osaka, all of Japan

[73] Assignee: Koei Chemical Co., Ltd., Osaka, Japan

[21] Appl. No.: 325,262

[22] PCT Filed: Feb. 18, 1994

[86] PCT No.: PCT/JP94/00254

§ 371 Date: Oct. 24, 1994

§ 102(e) Date: Oct. 24, 1994

[87] PCT Pub. No.: WO94/19328

PCT Pub. Date: Sep. 1, 1994

[30] Foreign Application Priority Data

Feb. 26, 1993 [JP] Japan .................................. 5-063461

[51] Int. Cl.⁶ .................................. C07D 241/18
[52] U.S. Cl. .................................. 544/406
[58] Field of Search .................................. 544/406

[56] References Cited

U.S. PATENT DOCUMENTS 3,646,031  2/1972  Abe et al. .................................. 544/406
4,962,111  10/1990  Welch et al. .................................. 544/405

OTHER PUBLICATIONS

Cynamon et al., *J. Med. Chem.* 35 p. 1212 (1992).
Imperial Chemical Industries, *Chemical Abstracts,* vol. 101, No. 155555 (1984).
Dalton et al, *Chemical Abstracts,* vol. 112, No. 40123 (1990).
Advanced Organic Chemistry by Jerry March (2nd Ed.), pp. 363–365, 367–368 (1977).

*Primary Examiner*—Emily Bernhardt
*Attorney, Agent, or Firm*—Armstrong, Westerman, Hattori, McLeland & Naughton

[57] ABSTRACT

This invention is to provide a pyrazine derivative capable of developing excellent therapeutic efficacy in infectious diseases caused by various acid-fast bacteria.

The pyrazine derivative of this invention is represented by the general formula

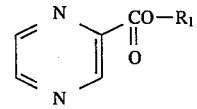

wherein $R_1$ is an octyl group or a pivaloyloxymethyl group.

3 Claims, No Drawings

PYRAZINE DERIVATIVES

This application is a 371 of PCT/JP94/00254 filed Feb. 18, 1994.

TECHNICAL FIELD

This invention relates to a novel pyrazine derivative and more particularly to a pyrazine derivative capable of exhibiting excellent therapeutic responses in infectious diseases caused by acid-fast bacteria, particularly *Mycobacterium tuberculosis* (briefly, *M. tuberculosis*), *Mycobacterium avium* (briefly, *M. avium*) and *Mycobacterium intracellulare* (briefly, *M. intracellulare*) and in mixed infections where two or more different kinds of such acid-fast bacteria are associated.

BACKGROUND ART

Pyrazinamide (or pyridinecarboxamide) is an antituberculosis agent which acts bactericidally against intracellular tubercle bacillus (*M. tuberculosis*), in particular. However, pyrazinamide has no antibacterial activity against other acid-fast bacteria such as *M. avium* and *M. intracellulare* and, therefore, is not expected to be effective against the *M. avium* complex which is becoming a more and more serious problem with the spread of AIDS. Therefore, even if acid-fast bacteria are detected in the patient by the Ziehl-Neelsen stain-microscopic examination of the sputum, no therapy can be immediately instituted and because of the need for differentiation as to whether the infection is associated with *M. tuberculosis* or due to the *M. avium* complex, a waiting time of several weeks is necessary for the institution of a therapy.

DISCLOSURE OF INVENTION

It is an object of this invention to provide a pyrazine derivative capable of exhibiting excellent antibacillar activity not only against *M. tuberculosis* but also against *M. avium* and *M. intracellulare*.

It is a further object of this invention to provide a pyrazine derivative capable of exhibiting excellent therapeutic efficacy in infectious diseases caused by an acid-fast bacteria, particularly *M. tuberculosis*, *M. avium* or *M. intracellulare*.

It is a still further object of this invention is to provide a pyrazine derivative capable of exhibiting excellent therapeutic efficacy in mixed infections caused by two or more different kinds of acid-fast bacteria, for example the mixed infection due to the *M. avium* complex.

It is still another object of this invention to provide a process for producing such pyrazine derivative.

Other features of this invention will become apparent as the following description proceeds.

The pyrazine derivative of this invention is a novel compound undisclosed in literature and can be represented by the following general formula (1)

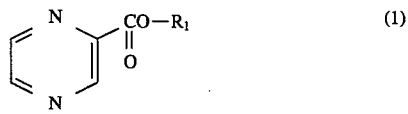

(1)

wherein $R_1$ represents an octyl group or a pivaloyloxymethyl group.

The pyrazine derivative of the above general formula (1) is a compound capable of exhibiting excellent therapeutic responses in infectious diseases caused by acid-fast bacteria, particularly *M. tuberculosis*, *M. avium* and *M. intracellulare*, and in mixed infections caused by two or more kinds of said acid-fast bacteria, for example the infection caused by the *M. avium* complex.

The compound of general formula (1) wherein $R_1$ is an octyl group, namely octyl pyrazinecarboxylate, can be produced by heating pyrazinecarboxylic acid and 1-octanol together in the presence of a strong acid.

The relative amounts of pyrazinecarboxylic acid and 1-octanol for use in the reaction are not particularly critical but it is generally recommendable to use 1–10 moles of the latter to each mole of the former. The reaction using a stoichiometric excess of 1-octanol can be carried out in the absence of a solvent but may optionally be conducted in a solvent, which may for example be an aromatic hydrocarbon such as benzene or toluene or an alicyclic ether such as tetrahydrofuran. The strong acid for use in this reaction can be liberally selected from among known acids. Thus, for example, inorganic acids such as sulfuric acid and hydrogen chloride can be mentioned. The amount of such strong acid is not so critical, but taking sulfuric acid as an example, it can be used in a proportion of generally 0.005–1 mole, preferably 0.01–0.2 mole, per mole of pyrazinecarboxylic acid. When hydrogen chloride is used, the reaction is preferably conducted by blowing 0.1–6 mole of hydrogen chloride per mole of pyrazinecarboxylic acid into the reaction system through a gas inlet. The above reaction proceeds well generally at 50°–150° C. and preferably at 70°–110° C. and goes to completion generally in about 3–10 hours. Though the objective octyl pyrazinecarboxylate can be obtained in a yield of 60% even without removing the byproduct water from the reaction system, the yield of the objective octyl pyrazine carboxylate can be improved by adding an agent forming an azeotropic mixture with the byproduct water, for example benzene, and by expelling the azeotrope from the reaction system.

Post-treatments following the above reaction can be carried out in the conventional manner. In an exemplary procedure, methylene chloride is added to the reaction mixture and, then, an aqueous solution of sodium carbonate is added. From the methylene chloride layer which separates, the methylene chloride is first distilled off and the residue is subjected to distillation under reduced pressure, whereby octyl pyrazinecarboxylate is isolated in pure form.

The compound of general formula (1) wherein $R_1$ is a pivaloyloxymethyl group, namely pivaloyloxymethyl pyrazinecarboxylate, can be produced by converting pyrazinecarboxylic acid to an alkali metal salt in the first place and, then, reacting this salt with chloromethyl pivalate which is readily available from commercial sources.

The process for producing pivaloyloxymethyl pyrazinecarboxylate is now described taking the use of the sodium salt as an example of said alkali metal pyrazinecarboxylate. Thus, pyrazinecarboxylic acid is dissolved in an aqueous solution containing an equimoler amount, with respect to the acid, of sodium hydroxide, water is then distilled off, and the residue is dried to give sodium pyrazinecarboxylate. To this sodium pyrazinecarboxylate is added 1–2 molar equivalents, with respect to sodium pyrazinecarboxylate, of chloromethyl pivalate, and, as the catalyst, 0.1–0.3 molar equivalent, with respect to sodium pyrazinecarboxylate, of a tertiary amine, e.g. triethylamine, and the reaction is conducted at 90°–120° C. for 3–10 hours, whereby pivaloyloxymethyl pyrazinecarboxylate is produced. As an alternative, pivaloyloxymethyl pyrazinecarboxylate can also be obtained without the aid of a catalyst by conducting the reaction in a solvent in which sodium pyrazinecarboxylate is at least partially soluble and which is inert to the reaction, for example dimethylformamide or N-methyl-2-pyrrolidone.

Post-treatments following the above reaction can be carried out in the conventional manner. By way of illustration, toluene is added to the reaction mixture at the end of the reaction and the precipitated sodium chloride is filtered off. From the filtrate the toluene is distilled off and the residue is subjected to distillation under reduced pressure, whereby pivaloyloxymethyl pyrazinecarboxylate is isolated in pure form.

BEST MODE OF CARRYING OUT THE INVENTION

The following production examples and test examples are intended to describe this invention in further detail and should by no means be construed as defining the scope of the invention. The $^1$H-NMR data presented in the following production examples were obtained by measurement using TMS as the internal standard and DMSO-$d_6$ as the solvent.

PRODUCTION EXAMPLE 1

A four-necked flask was charged with 100 g (0.768 mole) of 1-octanol and 10 g (0.081 mole) of pyrazinecarboxylic acid and while the internal temperature was maintained under stirring at 70°–80° C., 15 g (0.411 mole) of hydrogen chloride was introduced through a gas inlet tube over a period of 3 hours. Upon completion of the introduction of hydrogen chloride, the reaction mixture was cooled and 100 ml of methylene chloride was added. The mixture was transferred to a separatory funnel, in which it was washed with a small quantity of aqueous sodium carbonate solution. From the oil layer which separated, the methylene chloride was first distilled off and the residue was subjected to distillation under reduced pressure to give 11.5 g of octyl pyrazinecarboxylate. Yield: 60% (based on pyrazinecarboxylic acid)

Boiling point: 139°–140° C./2.5 mmHg $^1$H-NMR (ppm): 0.6–2.2 (15H, m, $(CH_2)_6CH_3$) 4.2–4.6 (2H, t, $OCH_2$) 8.7 (2H, s, pyrazine ring-H) 9.22 (1H, s, pyrazine ring-H) EIMS: m/e 236 ($M^+$)

PRODUCTION EXAMPLE 2

A four-necked flask was charged with 14.6 g (0.10 mole) of sodium pyrazinecarboxylate, 15.1 g (0.10 mole) of chloromethyl pivalate and 1.0 g (0.01 mole) of triethylamine and the charge was maintained under stirring at 98°–100° C. for 6 hours. The reaction mixture was then cooled and 100 ml of toluene was added. The solids (sodium chloride) were filtered off. From the filtrate thus obtained the toluene was distilled off and the filtrate was subjected to distillation under reduced pressure to give 17.2 g of pivaloyloxymethyl pyrazinecarboxylate. Yield: 72%

Boiling point: 135°–137° C./3.5 mmHg $^1$H-NMR (ppm): 1.2 (9H, s, tert-butyl) 6.03 (2H, s, $CH_2$) 8.7 (2H, s, pyrazine ring-H) 9.25 (1H, s, pyrazine ring-H)

CIMS (isobutane): m/e 239 ($M^+$ + H)

PRODUCTION EXAMPLE 3

A four-necked flask was charged with 426 g (3.271 mole) of 1-octanol, 100 g (0.806 mole) of pyrazinecarboxylic acid and 5.0 g (0.05 mole) of concentrated sulfuric acid and the internal temperature was maintained under stirring at 97°–100° C. for 8 hours. The reaction mixture was then cooled and transferred to a separatory funnel, in which it was washed with two portions, or a total of 330 g, of 8% aqueous solution of sodium carbonate. The oil layer which separated was washed with water and subjected to distillation under reduced pressure to give 168 g of octyl pyrazinecarboxylate. Yield: 88% (based on pyrazinecarboxylic acid).

PRODUCTION EXAMPLE 4

A four-necked flask was charged with 127.5 g (0.873 mole) of sodium pyrazinecarboxylate, 119.3 g (0.792 mole) of chloromethyl pivalate and 146 g of dimethylformamide and the internal temperature was maintained under stirring at 105°–110° C. for 8 hours. The reaction mixture was then cooled and transferred to a separatory funnel. After addition of 500 g of toluene, the mixture was washed with 3 portions, or a total of 900 g, of water. From the toluene layer which separated the toluene was first distilled off and the residue was subjected to distillation under reduced pressure to give 147 g of pivaloyloxymethyl pyrazinecarboxylate. Yield: 78% (based on chloromethyl pivalate).

TEST EXAMPLE 1

Assay of antibacterial activities against *M. avium* and *M. intracellulare*

First, 5.0 ml of Middlebrook 7H9 liquid medium (manufactured by Difco Laboratories) adjusted to pH 6 was taken in test tubes and the test compound was added at a final concentration of 200 γ/ml. The test compound was added as dissolved in dimethyl sulfoxide beforehand. Then, 0.1 ml of a bacterial cell suspension with a colony forming unit of $10^7$–$10^8$/ml and an optical density (briefly, OD) of 0.12 was added to the liquid medium and the mixture was maintained in an incubator at 37° C. for a predetermined time.

The test compounds used were octyl pyrazinecarboxylate, pivaloyloxymethyl pyrazinecarboxylate, and, as a reference compound, pyrazinamide. The control test was performed in the same manner. The OD values were determined by measuring the absorbance values with a turbidimeter at the wavelength of 640 nm. Two tubes were used for each determination and the OD value was calculated as the average.

The results of antibacterial activity assays against *M. avium* are shown in Tables 1 and 2 and the results of antibacterial activity assays against *M. intracellulare* are shown in Tables 3 and 4.

TABLE 1

| | Day 7 | | | Day 14 | | | Day 21 | | |
|---|---|---|---|---|---|---|---|---|---|
| | ΔOD | % | % | ΔOD | % | % | ΔOD | % | % |
| Control | 0.076 | 100 | | 0.142 | 100 | | 0.230 | 100 | |
| Pyrazinamide | 0.075 | 98.7 | 100 | 0.098 | 69.0 | 100 | 0.149 | 64.8 | 100 |
| Octyl pyrazinecarboxylate | 0.014 | 18.7 | 18.4 | 0.011 | 7.7 | 11.2 | 0.013 | 5.7 | 8.7 |

TABLE 2

|  | Day 7 | | | Day 14 | | | Day 21 | | |
| --- | --- | --- | --- | --- | --- | --- | --- | --- | --- |
|  | ΔOD | % | % | ΔOD | % | % | ΔOD | % | % |
| Control | 0.085 | 100 |  | 0.166 | 100 |  | 0.258 | 100 |  |
| Pyrazinamide | 0.079 | 92.9 | 100 | 0.106 | 63.9 | 100 | 0.173 | 67.1 | 100 |
| Pivaloyloxymethyl pyrazine-carboxylate | 0.000 | 0.0 | 0.0 | 0.009 | 5.4 | 8.5 | 0.081 | 31.4 | 46.8 |

TABLE 3

|  | Day 7 | | | Day 14 | | | Day 21 | | |
| --- | --- | --- | --- | --- | --- | --- | --- | --- | --- |
|  | ΔOD | % | % | ΔOD | % | % | ΔOD | % | % |
| Control | 0.255 | 100 |  | 0.495 | 100 |  | 0.660 | 100 |  |
| Pyrazinamide | 0.230 | 90.2 | 100 | 0.458 | 92.5 | 100 | 0.600 | 90.9 | 100 |
| Octyl pyrazinecarboxylate | 0.012 | 4.7 | 5.2 | 0.012 | 2.4 | 2.6 | 0.021 | 3.2 | 3.5 |

TABLE 4

|  | Day 7 | | | Day 14 | | | Day 21 | | |
| --- | --- | --- | --- | --- | --- | --- | --- | --- | --- |
|  | ΔOD | % | % | ΔOD | % | % | ΔOD | % | % |
| Control | 0.279 | 100 |  | 0.515 | 100 |  | 0.650 | 100 |  |
| Pyrazinamide | 0.252 | 90.3 | 100 | 0.480 | 93.2 | 100 | 0.620 | 95.4 | 100 |
| Pivaloyloxymethyl pyrazine carboxylate | 0.000 | 0.0 | 0.0 | 0.000 | 0.0 | 0.0 | 0.000 | 0.0 | 0.0 |

In Tables 1 to 4 above, ΔOD represents the amount of increase in OD from the value before the test. Further, % represents ΔOD of the compound of this invention (octyl pyrazinecarboxylate or pivaloyloxymethyl pyrazinecarboxylate), based on ΔOD of control or pyrazinamide calculated as 100.

TEST EXAMPLE 2

Assay of antibacterial activity against *M. tuberculosis*

The antibacterial activity against *M. tuberculosis* $H_{37}$ Rv was assayed in the same manner as Test Example 1. The results are shown in Table 5.

TABLE 5

|  | Concentration of test compound γ/ml | ΔOD on day 21, based on the ΔOD of control taken as 100 |
| --- | --- | --- |
| Octyl pyrazine-carboxylate | 500 | 0.5 |
|  | 250 | 12.3 |
|  | 125 | 56.9 |
| Pivaloyloxymethyl pyrazinecarboxylate | 500 | 0.8 |
|  | 250 | 1.3 |
|  | 125 | 0.3 |

It is apparent from Tables 1 to 5 that the compound of this invention is capable of producing excellent therapeutic responses in infectious diseases caused by *M. tuberculosis*, *M. avium* and *M. intracellulare*.

What is claimed is:

1. A pyrazine compound of the formula

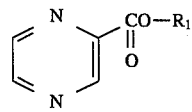

wherein $R_1$ represents an octyl group or a pivaloyloxymethyl group.

2. The pyrazine compound according to claim 1 wherein $R_1$ is an octyl group.

3. The pyrazine compound according to claim 1 wherein $R_1$ is a pivaloyloxymethyl group.

* * * * *